US006835196B2

(12) United States Patent  
Biedermann et al.

(10) Patent No.: US 6,835,196 B2
(45) Date of Patent: Dec. 28, 2004

(54) ANCHORING ELEMENT

(75) Inventors: Lutz Biedermann, VS-Villingen (DE); Jürgen Harms, Karlsruhe (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 63 days.

(21) Appl. No.: 10/040,703

(22) Filed: Jan. 7, 2002

(65) Prior Publication Data

US 2002/0143341 A1 Oct. 3, 2002

(30) Foreign Application Priority Data

Mar. 27, 2001 (DE) .......................................... 101 15 014

(51) Int. Cl.$^7$ ............................................... A61B 17/56
(52) U.S. Cl. ........................................ 606/61; 606/73
(58) Field of Search ............................. 606/61, 72, 73

(56) References Cited

U.S. PATENT DOCUMENTS

| 1,410,480 A | | 3/1922 | Landgraf | |
| 5,167,664 A | | 12/1992 | Hodorek | 606/73 |
| 5,443,467 A | * | 8/1995 | Biedermann et al. | 606/65 |
| 5,527,314 A | * | 6/1996 | Brumfield et al. | 606/61 |
| 5,545,165 A | * | 8/1996 | Biedermann et al. | 606/61 |
| 5,672,176 A | * | 9/1997 | Biedermann et al. | 606/61 |
| 5,681,319 A | * | 10/1997 | Biedermann et al. | 606/104 |
| 5,716,356 A | * | 2/1998 | Biedermann et al. | 606/61 |
| 5,961,517 A | * | 10/1999 | Biedermann et al. | 606/61 |
| 6,074,391 A | * | 6/2000 | Metz-Stavenhagen et al. | 606/61 |
| 2002/0058942 A1 | * | 5/2002 | Biedermann et al. | 606/73 |
| 2002/0082602 A1 | * | 6/2002 | Biedermann et al. | 606/61 |

FOREIGN PATENT DOCUMENTS

| DE | 43 07 571 C1 | 4/1994 |
| DE | 199 36 286 A1 | 3/2001 |
| EP | 0 933 065 A1 | 8/1999 |
| FR | 2 720 923 | 12/1995 |
| FR | 2 786 088 | 5/2000 |
| WO | WO 94/00066 | 1/1994 |
| WO | WO 99/48431 | 9/1999 |
| WO | WO 01/03593 A1 | 1/2001 |
| WO | Wo 01/08574 | 2/2001 |

* cited by examiner

Primary Examiner—Eduardo C. Robert
Assistant Examiner—D. Austin Bonderer
(74) Attorney, Agent, or Firm—George W. Neuner; Edwards & Angell LLP

(57) ABSTRACT

An anchoring element with a screw (12) comprising a threaded section (13) and a head (15) designed as a spherical segment-shaped section, and with a receiving portion (1) for connecting the screw (12) to a rod (19), is provided. The receiving portion (1) comprises a first end (2) and a second end (3) opposite the latter and a longitudinal axis (4) passing through the two ends (2, 3). The receiving portion further comprises a bore (5) coaxial with the longitudinal axis (4), a first region adjoining the first end (2) with an essentially U-shaped cross-section (18) with two free arms (8, 9) comprising a thread for receiving the rod (19) to be inserted, a region adjoining the other end (3) for receiving the head (15), and an element which exerts pressure on the rod (19) or on the head (15). In order that the screws can be used in situ for very different lengths, the threaded section (13) and the head (15) are designed as separate parts.

13 Claims, 4 Drawing Sheets

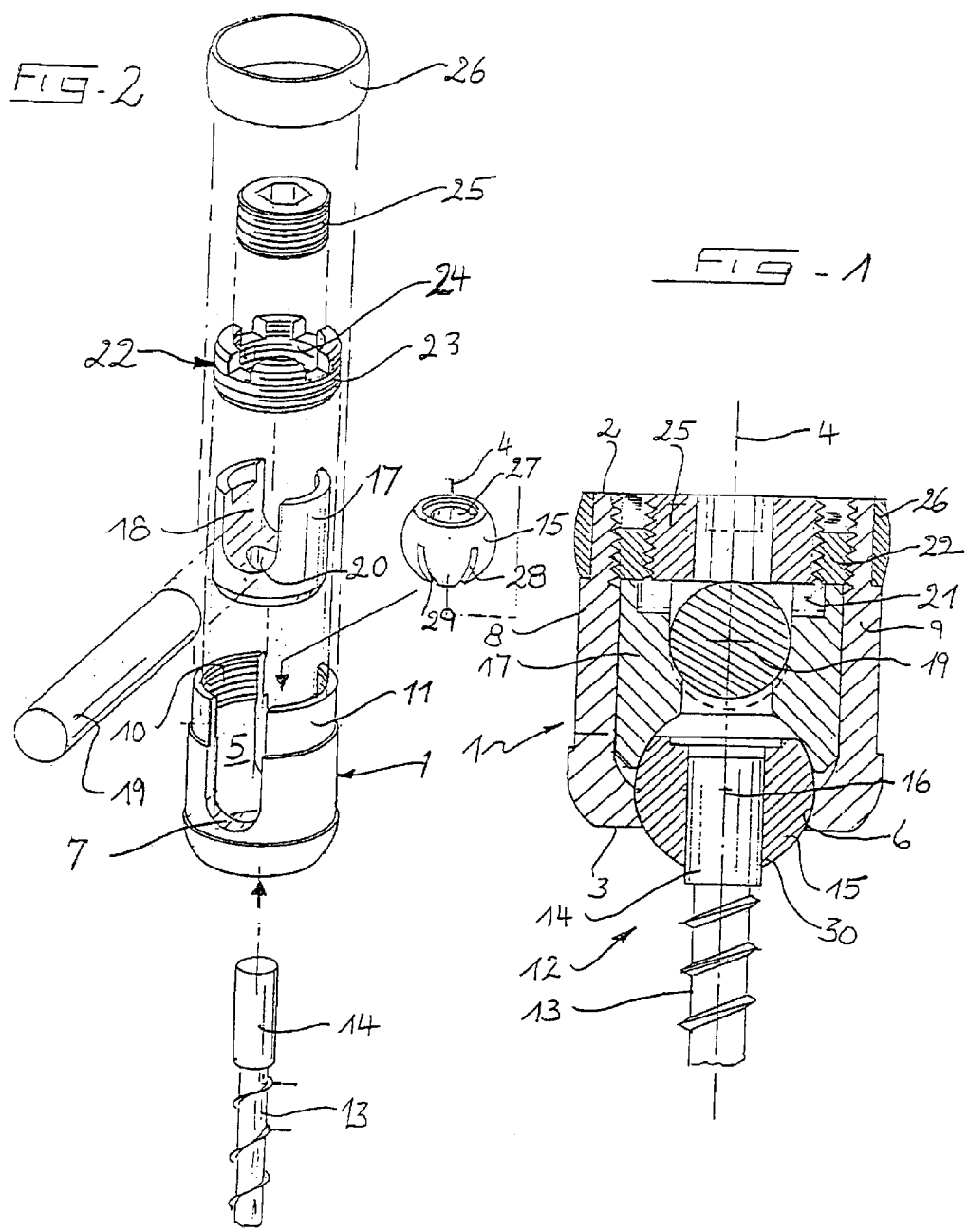

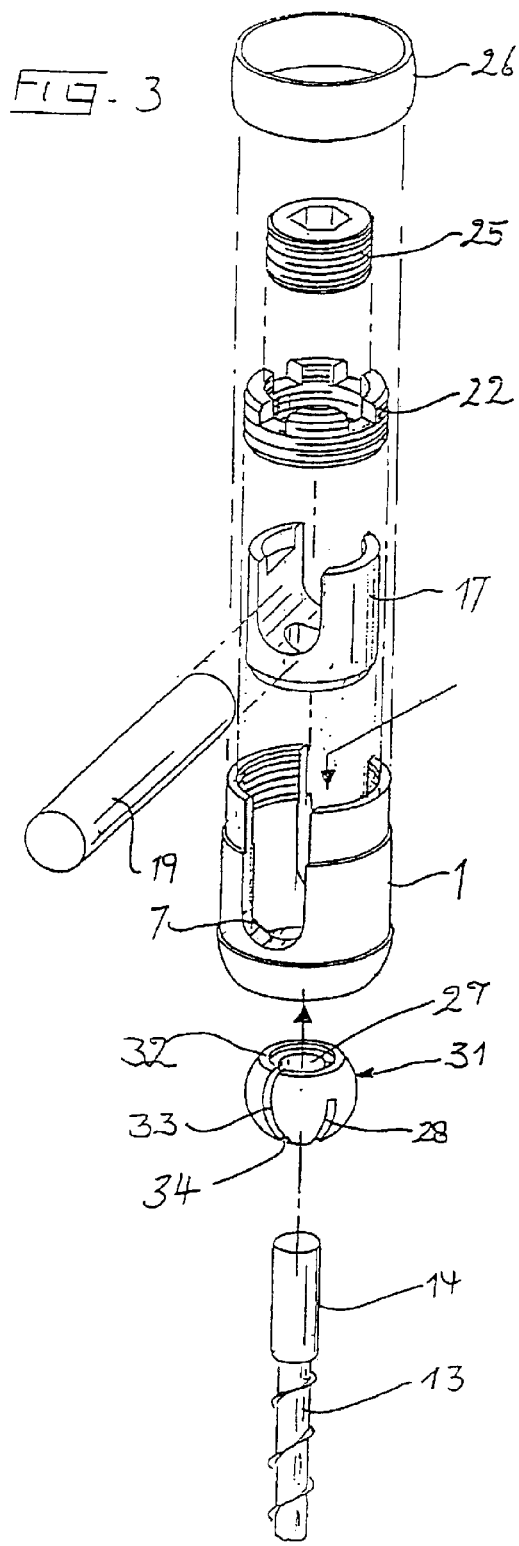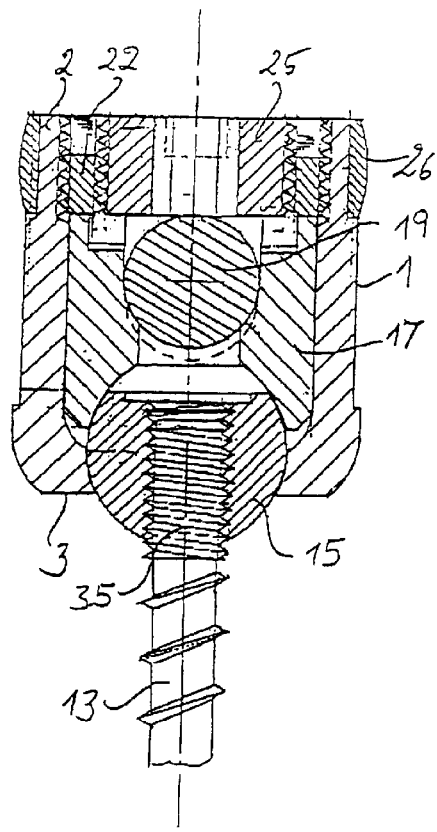

ANCHORING ELEMENT

FIELD OF THE INVENTION

The invention concerns an anchoring element with a screw comprising a threaded section and a head designed as a spherical segment-shaped section, and with a receiving portion for connecting the screw to a rod. An anchoring element of this kind is used in particular in vertebral column surgery, but also in accident surgery on other bones.

BACKGROUND OF THE INVENTION

Such an anchoring element is known from DE 43 07 576 C1, for example. With known anchoring elements and screws of this kind, the threaded section of the screw and its head are constructed in one piece. As the surgeon needs very different lengths of screws, he must always have different sets of such screws available. This makes a considerable stockpile necessary, resulting in considerable costs.

It is the object of the invention to eliminate this drawback.

SUMMARY OF THE INVENTION

This object is achieved by an anchoring element with a screw (12) comprising a threaded section (13) and a head (15) designed as a spherical segment-shaped section, and with a receiving portion (1) for connecting the screw (12) to a rod (19), wherein the receiving portion (1) comprises a first end (2) and a second end (3) opposite the latter, a longitudinal axis (4) passing through the two ends (2, 3), a bore (5) coaxial with the longitudinal axis (4), a firs t region adjoining the first end (2) with an essentially Us shaped cross-section (7) with two free arms (8, 9) comprising a thread for receiving the rod (19) to be inserted, a region adjoining the other end (3) for receiving the head (15), and an element (22, 17) which exerts pressure on the rod (19) or on the head (15), characterised in that the threaded section (13) and the head (15) are designed as separate parts.

As a r result it is possible for the surgeon during application to shorten the threaded section to a desired length before or after implanting, and then connect it to the head and the receiving portion. In this way the maintenance of stocks is substantially reduced, and at the same time the possibilities for the Burgeon to make finer adjustments are increased, as the screws can be shortened to any length.

Further embodiments of the invention include one or more of the following features:

- the threaded section (13) comprises a shank (14) at the head end;
- the head (15) comprises a spring-yielding edge on its side facing towards the threaded section (13);
- the edge (34) facing towards the threaded section comprises one or more apertures or recesses (28, 29, 33) which are directed parallel to the axis of symmetry (4) and distributed circumferentially;
- an aperture (33) extends over the whole wall length, seen in a direction parallel to the axis of symmetry (4);
- the head (15) comprises a bore (27) coaxial with the axis of symmetry;
- the bore (27) is cylindrical;
- the shank (14) comprises a rough surface;
- the shank (14) is polygonal;
- the head (15) comprises an internal thread in the bore and the shank (35) comprises an external thread mating therewith; and/or
- the head (15) is corrugated in the circumferential direction in the bore and the shank (37) comprises a corresponding corrugation on its outer side.

Further characteristics and suitabilities of the invention are apparent from the description of practical examples with the aid of the figures.

BRIEF DESCRIPTION OF THE DRAWINGS

The figures show:

FIG. 1 a side view of a first embodiment in section;

FIG. 2 the embodiment shown in FIG. 1 in an exploded view;

FIG. 3 a corresponding exploded view of a second embodiment;

FIG. 9 a side view of a further embodiment in section;

DETAILED DESCRIPTION OF THE INVENTION

Figure 4:
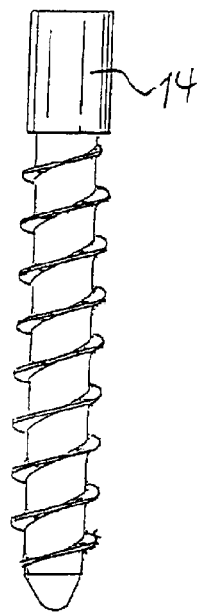
FIG. 4 a side view of the first bone screw used in both embodiments.

In the first embodiment shown in FIGS. 1 and 2, the anchoring element comprises a receiving portion 1 of cylindrical construction with a first end 2 and an opposed second end 3. The two ends extend perpendicularly to an axis of symmetry or longitudinal axis 4. Coaxially with the longitudinal axis 4 is provided a first coaxial bore 5 which extends from the first end 2 and which extends as far as a predetermined distance from the second end 3. At the second end 3 is provided a second bore whose diameter is smaller than the diameter of the first bore. In the practical example shown, the second bore is designed as an opening whose edge is shaped as a hollow spherical segment-shaped section whose centre is directed towards the first end 2.

The receiving portion 1 comprises, starting from the first end 2, a U-shaped recess 7 extending perpendicularly to the longitudinal axis 3, with two free arms 8, 9 ending towards the first end 2. Adjoining the first end 2, the arms comprise an internal thread 10. The bottom of the U-shaped recess extends as far as a predetermined distance from the second end 3. Adjoining the first end 2, the arms 8, 9 comprise on the outside a section 11 whose outside diameter is smaller than the outside diameter of the adjoining section of the receiving portion.

The screw 12 cooperating with the receiving portion 1 comprises a threaded section 13 designed as a bone screw and a spherical segment-shaped head 15 which is connected thereto in the assembled view shown in FIG. 1. The head has a radius which is such that, when the head 15 is received in the second bore 6 as shown in FIG. 1, the head mates with a hollow spherical segment-shaped wall section formed there, wherein the hollow spherical segment-shaped section is designed in such a way that the centre 16 of the sphere is offset towards the first end 2 to such an extent that the section forms an abutment and the sphere or the head 15 is held in the hollow spherical segment-shaped section of the second bore 6.

There is further provided a pressure element 17 which is of cylindrical construction and has an outside diameter which is so large that the pressure element can be introduced into the first bore 5 and moved to and fro in the axial direction in the latter. On its lower side facing towards the second end 3 the pressure element 17 comprises a hollow spherical segment-shaped section which is constructed symmetrically to the longitudinal axis 4 and whose radius corresponds to the radius of the head 5. The pressure element comprises a U-shaped recess 18 which extends transversely to the longitudinal axis 4 and whose free arms extend towards the first end 2. The lateral diameter of this U-shaped recess is selected so that a rod 19 to be received can be inserted in the recess and guided laterally in the latter. The depth of the hollow spherical segment-shaped recess is selected so that it ends at a distance from the second end 3 which is greater than the distance from the centre 16 corresponding to the radius of the head 15, looking towards the first end 2. At the bottom of the U-shaped recess 18 is an adjoining coaxial bore 20 whose diameter is smaller than the diameter of the rod 19 to be received.

As can be seen from FIG. 1, the U-shaped recess 18 comprises, at its end directed towards the first end 2, a section 21 whose inside width is greater than the diameter of the U-shaped recess 18.

On the side facing towards the first end 2, the pressure element 17 is adjoined by a nut 22 which comprises an external thread 23 mating with the internal thread 10 and in addition an internal thread 24. The inside dimensions of the nut 22 are selected so that the inside width is smaller than the diameter of the section 21 and larger than the diameter of the rod 19 and hence of the U-shaped recess 18. Further, an internal nut 25 with an external thread mating with the internal thread 24 is provided. Finally, there is provided a bush 26 which encompasses the free end adjoining the first end 2 and which in the assembled state sits on the annular section 11, as shown in FIG. 1.

As can best be seen from FIG. 2, the nut 22 comprises a slot and the internal nut 25 comprises a hexagon opening for respective separate application of screwdrivers.

As can best be seen from FIG. 2, the head 15 is designed as a sphere flattened at its end which is to face towards the first end 2, and comprises a bore 27 coaxial with the longitudinal axis 4. The diameter of the bore 27 is equal to the outside diameter of the shank 14 and designed in such a way that the shank can be inserted in the bore with frictional locking. As can be seen from FIG. 2, the hollow spherical segment-shaped element shaped in this way is provided, on its side opposite the flattened end, with sections 28, 29 which are spaced apart from each other in the circumferential direction and extend parallel to the longitudinal axis 4 and extend as far as the end opposite the flattened side. As a result, the edge 30 facing away from the first end 2 is designed to be capable of spring yielding outwards for introduction of the shank 14.

In operation, first the screw 12 is screwed into the bone or vertebra. For this purpose the shank 14 has known engagement possibilities such as a hexagon socket. Then the surgeon shortens the shank 14 to the desired length and first places the receiving portion with the second bore on the shank 14 and then guides the head from the first end 2 onto the shank 14, so that the shank 14 is introduced into the bore 27 from the spring-yielding edge 30 and the head surrounds the shank in the manner shown in FIG. 1. The head 15 and the shank 14 are connected to each other with frictional locking. Next the pressure element 17 is inserted and, by screwing in the nut 22, pressed onto the head 15 in such a way that the latter undergoes desired rotational stabilisation. The bush 26 is fitted and then by means of the internal nut 25 the rod 19 is fixed. The rod 19 exerts an additional pressure on the head 15 via the pressure element 17.

Due to the pressure on the head 15 exerted as seen from the first end 2, the slotted head 15 is on the one hand connected or clamped to the shank 14, preventing movement, and at the same time the head is locked in its rotational position.

The second embodiment shown in FIG. 3 differs from the embodiment described above in a modified head 31. The latter comprises, as in the first embodiment, notches 28 which are offset from each other in the circumferential direction and which end free at the edge 34 facing away from the first end and are at a distance from the edge 32 facing towards the first end 2. However, a notch 33 which extends fully from the edge 32 to the opposite edge 34 is provided, with the result that the spherical segment formed in this way can be compressed by an amount defined by the width of the notch 33. The width of the slot 33 formed in this way is selected so that the head 31 first of all can be compressed to such an extent that it can be pressed in the direction shown in FIG. 3 from the second end 2 into the first bore 5 and that then the shank 14 can be inserted in the head in the same way as described above and in the same way is held in the clamped position.

Figure 6:
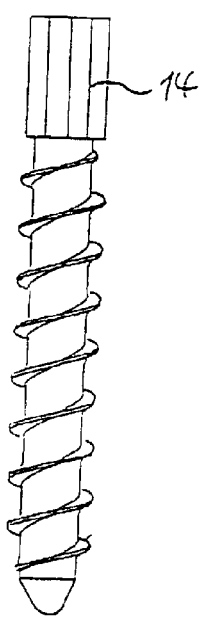
FIG. 6 a side view of a second embodiment of the bone screw used in the first two practical examples.
Figure 8:
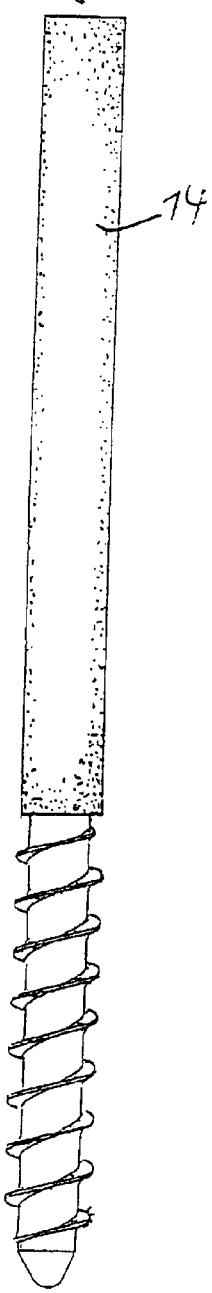
FIG. 8 a side view of a third embodiment of a bone screw shown in the first two practical examples.
Figure 5:
FIG. 5 a top view of the bone screw in FIG. 4.
Figure 7:
FIG. 7 a top view of the bone screw shown in FIG. 6.

The shank 14 of the screw preferably has the cylindrical shape shown in FIGS. 4 and 5 or a polygonal shape shown in FIGS. 6 and 7. In the latter the cross section is octagonal. A further preferred embodiment is shown in FIG. 8. The shank is cylindrical here and comprises a rough surface which facilitates engagement between sphere 15 and shank.

The further embodiment shown in FIG. 9 corresponds to the preceding practical examples in all characteristics concerning the receiving portion 1, the pressure element 17, the rod 19 and the screws 22 and 25. The only difference lies in that the head 15 is designed as a spherical segment which in its external dimensions corresponds to the two preceding spherical segments, but has no notches 28 or 33. Instead, the spherical segment has an internal thread on the inside of its bore 27. Instead of the shank 14, there is provided a shank 35 with a thread which is designed to mate with the internal thread of the head. The bore is designed as a blind bore which ends at the end facing towards the free end 2 or comprises a stop there, so that the screw can be screwed only so far into the position shown in which it does not protrude from the spherical segment on its flattened side. As shown in FIG. 9, the internal thread of the head 15 and the corresponding external thread of the shank 35 are formed in the direction preferably opposite the direction of the thread of the threaded section 13 of the bone screw.

Operation takes place in the same manner as in the practical example described first, wherein after shortening of the shank 35 the head 15 is introduced into the bore 5 from the first end 2 of the receiving portion 1 and screwed onto the shank 35 introduced from the second end 3.

Figure 10:
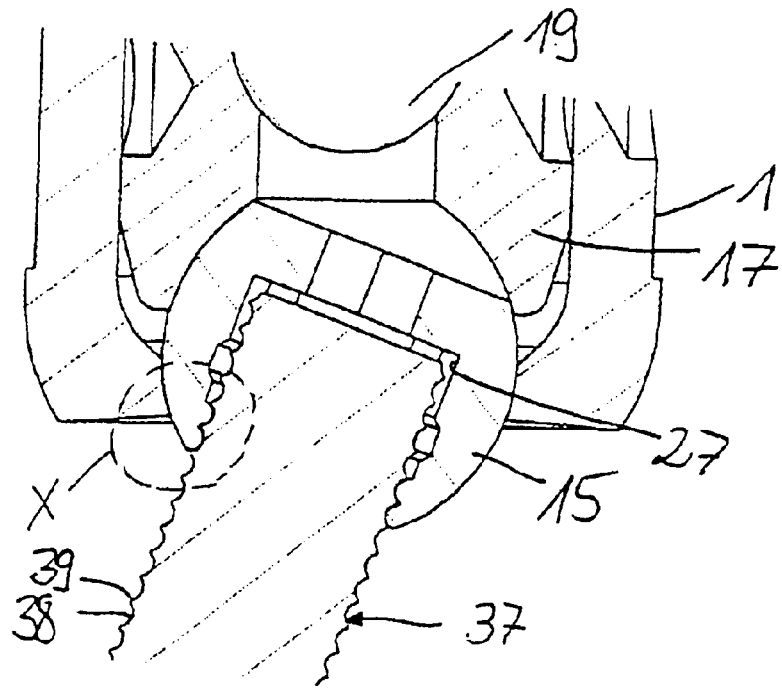
FIG. 10 a side view of a further embodiment in section.
Figure 11:
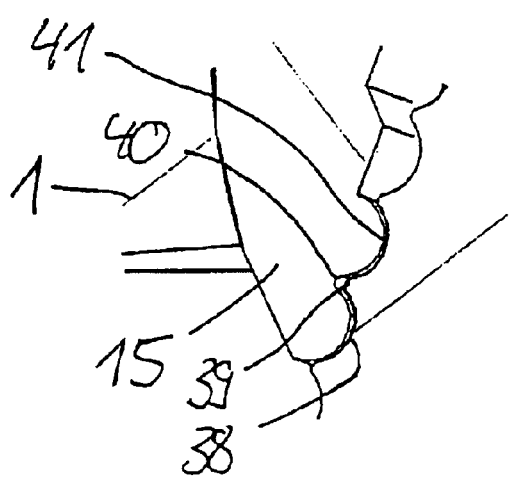
FIG. 11 an enlarged view of the detail X of FIG. 10.

The further embodiment shown in FIGS. 10 and 11 corresponds to the preceding practical examples in all characteristics concerning the receiving portion 1, the pressure element 17, the rod 19 and the screws 22 and 25. Instead of the shank 35 and the head 15 of the embodiment according to FIG. 9, which comprises the cooperating threads, in this embodiment the shank 37 is designed as a corrugated rod in a section adjoining the end opposite the bone threaded section. The outer surface of the shank comprises valleys 38 running in the circumferential direction and ridges 39 in between them. The valleys 38 have, seen in the circumferential direction, a circle segment-shaped cross-section and their diameter halfway up or down is much larger than the corresponding diameter of the crest 39, so that the crests 39 are pointed in relation to the bottom of the valleys 38. The head 15 is designed as a spherical segment which in its external dimensions corresponds to the spherical segments mentioned above, but which has no notches 28 or 33. On the inside of its bore 27, the spherical segment of the head 15 comprises corrugations running in the circumferential direction with valleys 40 and ridges 41 which correspond to the ridges 39 and valleys 38 of the shank 37 respectively. Between the valleys 38 and the ridges 39 of the shank on the one hand and the corresponding ridges 40 and valleys 41 on the other hand is a small gap, so that the shank can be introduced into the spherical segment.

Operation takes place in a similar manner to the practical example according to FIG. 9. Shortening of the corrugated shank 37 is however easier in this embodiment than shortening of the shank 35 with the thread according to FIG. 9, as the valleys 38 allow easy cutting off, whereas with the shank 35 with the thread according to FIG. 9 care must be taken that the thread is not destroyed. After shortening of the shank 37, the head 15 is introduced into the bore 5 from the first end 2 of the receiving portion 1 and pressed onto the shank 37. In the process the corrugations of the shank 37 and the corresponding ones of the bore 27 of the head 15 cooperate, so that the shank is held.

In the practical examples described above, the head 15 is in each case held by an edge designed in one piece with the receiving portion 1. Such an abutment can also be formed in another way: for example, it is possible to drill the first bore 5 completely through the receiving portion 1 and then, adjoining the second end, to mount in it a holding element which receives the head 15.

In the practical examples described above, the receiving portion always comprises the nut 22 and an internal nut 25 as well as a bush 26. This fixing can also be designed differently in a known manner. In particular, if occasion arises only an internal nut can be provided.

In the practical example described above with reference to FIG. 9, the head 15 has no notches 28, 33. In a further embodiment, head 15 and shank 35 have, as in the view shown in FIG. 9, threads mating with each other. The head 15 however comprises in addition the notch 33 extending over the whole length so that, as in the embodiment shown in FIG. 3, the head without the shank screwed in can be inserted in the receiving portion from the edge 3 by compression and then fitted on the shank 35 which can also be introduced from the end 3, by screwing in, and connected to the shank 35. As a result of the slot, when the pressure elements are applied or when the pressure is exerted on the head 15, at the same time the head and the shank 35 are compressed more firmly than without such a slot.

In a further embodiment, notches 28 can be provided additionally in the manner shown in FIG. 3, in order thus to cause even greater contact pressure with the threaded shank 35.

What is claimed is:

1. An anchoring element comprising:
    a screw;
    a receiving portion for connecting the screw to a rod;
    wherein the screw comprises a threaded section and a head having an exterior surface with a spherical segment-shaped section;
    wherein the receiving portion comprises a first end, a second end opposite the first end, a longitudinal axis passing through the two ends, a bore coaxial with the longitudinal axis, a first region adjoining the first end with an essentially U-shaped cross-section with two free arms for receiving the rod to be inserted, the two free arms comprising a thread, a second region adjoining the second end for receiving the spherical segment-shaped section of said head; and
    an element which exerts pressure on the rod or on the head;
    wherein the thread section and the spherical segment-shaped section of the head of the screw are separate parts.

2. The anchoring element according to claim 1, wherein the threaded section comprises a shank for engaging the head.

3. The anchoring element according to claim 2, wherein the head comprises a spring-like yielding edge facing toward the threaded section of the screw.

4. The anchoring element according to claim 3, wherein the spring-like yielding edge comprises one or more apertures or recesses which are directed parallel to the as and distributed circumferentially around the head.

5. The anchoring element according to claim 2, wherein the shank comprises the rough surface.

6. The anchoring element according to claim 2, wherein the shank has a polygonal cross sectional shape in a section perpendicular to the axis.

7. The anchoring element according to claim 1, wherein the head comprises a side wall and a bore hole coaxial with the axis.

8. The anchoring element according to claim 7, wherein the head contains an aperture extending over an entire length of the side wall in a direction parallel to the axis.

9. The anchoring element according to claim 7, wherein the bore is cylindrical.

10. An anchoring element comprising:
    a screw;
    a receiving portion for connecting the screw to a rod;
    wherein the screw comprises a threaded section and a head having a spherical segment-shaped section;
    wherein the receiving portion comprises a first end, a second end opposite the first end, a longitudinal axis passing through the two ends, a bore coaxial with the longitudinal axis, a first region adjoining the first end with an essentially U-shaped cross-section with two free arms for receiving the rod (19) to be inserted, the two free arms comprising a thread, a second region adjoining the second end for receive the spherical segment-shaped section of said head; and
    an element which exerts pressure on the rod or on the head;
    wherein the thread section and the head of the screw are separate parts;
    wherein the head comprises a side wall and a bore hole coaxial with the axis;
    wherein the bore hole has an internal thread and the shank has an external thread for mating therewith.

11. The anchoring element according to claim 7, wherein the bore hole is corrugated internally in the circumferential direction and the shank has a corresponding corrugation on its outer side for mating therewith.

12. An anchoring element comprising:

a screw;

a receiving portion for connecting the screw to a rod;

wherein the screw comprises a threaded section and a head having an exterior surface with a spherical segment-shaped section;

wherein the receiving portion comprises a first end, a second end opposite the first end, a longitudinal axis passing through the two ends, a bore coaxial with the longitudinal axis, a first region adjoining the first end with an essentially U-shaped cross-section with two free arms for receiving the rod to be inserted, the two free arms comprising a thread, a second region adjoining the second end for receiving the spherical segment-shaped section of said head; and a pressure element which exerts pressure on the rod or on the head;

wherein the thread section and the head of the screw are separate parts, thereby permitting adjustment of the length of the screw after placement of the screw in bone tissue.

13. An anchoring element comprising:

a screw;

a receiving portion for connecting the screw to a rod;

wherein the screw comprises a threaded section and a head having an exterior surface with a spherical segment-shaped section;

wherein the receiving portion comprises a first end, a second end opposite the first end, a longitudinal axis passing through the two ends, a bore coaxial with the longitudinal axis, a first region adjoining the first end with an essentially U-shaped cross-section with two free arms for receiving the rod to be inserted, the two free arms comprising a thread, a second region adjoining the second end for receiving the spherical segment-shaped section of said head; and a pressure element which exerts pressure on the rod or on the head;

wherein the thread section and the head of the screw are separate parts;

wherein the threaded section comprises a shank for engaging the head;

wherein pressure exerted by the pressure element fixes the head to the shank, preventing movement and locking a rotational position.

* * * * *